United States Patent [19]

McDonough et al.

[11] Patent Number: 5,126,250

[45] Date of Patent: Jun. 30, 1992

[54] METHOD FOR THE REDUCTION OF HETEROGENEITY OF MONOCLONAL ANTIBODIES

[75] Inventors: James P. McDonough, Bloomington; Thomas C. Furman, Indianapolis, both of Ind.; Richard M. Bartholomew; Rodney A. Jue, both of San Diego, Calif.

[73] Assignees: Eli Lilly and Company, Indianapolis, Ind.; Hybritech Incorporated, San Diego, Calif.

[21] Appl. No.: 364,056

[22] Filed: Jun. 9, 1989

Related U.S. Application Data

[63] Continuation-in-part of Ser. No. 250,786, Sep. 28, 1988, abandoned, and Ser. No. 250,787, Sep. 28, 1988, abandoned, and Ser. No. 250,788, Sep. 28, 1988, abandoned.

[51] Int. Cl.⁵ .................... C12P 21/06; C12P 21/08
[52] U.S. Cl. .................... 435/68.1; 435/69.1; 435/69.5; 435/272; 435/240.27; 530/402; 530/388.1; 530/387.3; 530/388.15
[58] Field of Search ............ 435/69, 68, 272, 240.27, 435/68.1, 69.1; 530/389, 391, 402

[56] References Cited

U.S. PATENT DOCUMENTS 4,604,235  8/1986  Flashner ........................ 530/387
4,801,687  1/1989  Ngo ............................. 530/387

OTHER PUBLICATIONS

Ostlund, C., 1986, Tibtech, Nov. 288-293.
Karl et al., 1988, Abstract from the American Chemical Society National Meeting, Los Angeles, Calif., USA, Sep. 25-30.
Tucker et al., 1979, Science 206:1299-1303.
Talbot et al., 1985, J. Immun. Methods 79:283-291.
Lee et al., 1986, J. Biotech. 4:189-204.
Carlsson et al., 1985, J. Immun. Methods 79:89-98.
Butler et al., 1987, Mol. Immun. 24:1317-1326.
Heyermann et al., 1987, Mol. Immun. 24:1327-1334.
Breddam, K., 1986, Carlsberg Res. Commun. 51:83, 112-113.
McDonough et al., 1989, Abstract and Data from a Poster presented at the UCLA Symposium on Protein Engineering. Jan. 17 through Jan. 22.
Sigma Catalogue, 1989, p. 392.

*Primary Examiner*—Sam Rosen
*Attorney, Agent, or Firm*—Douglas K. Norman; Leroy Whitaker

[57] ABSTRACT

Novel methods for reducing the heterogeneity of secreted monoclonal antibodies are disclosed. The first method comprises incubating the heterogeneous antibodies at low pH for a length of time sufficient to convert the heterogeneous forms of antibodies into substantially homogeneous forms. Another method produces the same result using ascites fluid, while yet another method produces the same result using carboxypeptidase. The homogeneous antibodies can then be purified in high yield.

63 Claims, 1 Drawing Sheet

METHOD FOR THE REDUCTION OF HETEROGENEITY OF MONOCLONAL ANTIBODIES

CROSS-REFERENCE TO RELATED APPLICATIONS

This application is a continuation-in-part application of copending U.S. patent application Ser. No. 07/250,786, filed Sep. 28, 1988; copending U.S. patent application Ser. No. 07/250,787, filed Sep. 28, 1988 and copending U.S. patent application Ser. No. 07/250,788, filed Sep. 28, 1988, all now abandoned.

SUMMARY OF THE INVENTION

The large scale production of monoclonal antibodies from hybridoma cells has triggered a revolution in the prognosis, diagnosis and treatment of various disease states. Monoclonal antibodies are also useful in determining the stages of various natural conditions, such as pregnancy. It has been discovered, however, that many hybridoma-derived antibodies display heterogeneous forms which greatly hinder the purification and isolation processes needed to attain high yields from the production strains. Cation exchange chromatography demonstrates that there are at least three discrete heterogeneous forms of antibody secreted from cells grown in vitro. These forms may appear in varying relative amounts. These heterogeneous forms are not found to the same degree in ascites-derived antibodies, yet the production of high levels of antibodies from ascites is far too cumbersome and expensive for commercial purposes.

The biochemical basis for this heterogeneity arises from the presence of an extra amino acid or acids attached to the carboxy terminus of the antibody heavy chains. The terminal amino acid is, most likely, usually removed during the internal processing or secretion of the antibody from the cell, as the inferred amino acid sequence derived from the DNA sequence of the antibody gene does contain an extra amino acid. One of the three heterogeneous forms is an antibody which contains no extra terminal amino acid on either of its heavy chains. The second of the three discrete heterogeneous forms contains an extra amino acid on one of its heavy chains, while the third form contains extra amino acids on both heavy chains.

The present invention comprises a method for specifically cleaving the extra amino acid from the heavy chains of the heterogeneous antibodies of any isotype, thereby converting all three forms into one, substantially pure, homogeneous mixture. The development and exploitation of monoclonal antibody technology depends upon the availability of large volumes of substantially homogeneous antibodies. This development has been somewhat retarded by the inability to easily purify and characterize the various heterogeneous forms of secreted antibodies. The present invention is useful and especially important in that it allows for the conversion of most heterogeneous antibodies into one substantially homogeneous form before purification. This conversion leads to a higher yield of antibody with more defined biochemical characteristics, as well as a decrease in purification contamination with heterogeneous forms of antibody. Furthermore, the possession of highly purified single-form antibodies greatly increases the reproducibility and consistency of subsequent modifications, such as immunoconjugation or immobilization reactions.

For purposes of the present invention, as disclosed and claimed herein, the following terms are defined below:

Antibody-producing cell—any cell, transformed formed cell or hybridoma which produces antibodies, either in vitro or in vivo.

Ascites Fluid—the fluid drained from the peritoneal cavity of an animal infected with an ascites tumor.

CP—carboxy peptidase.

CPIP ratio—the carboxypeptidase enzyme units/milligram immunoglobulin protein ratio.

Culture Fluid—any fluid which contains antibodies, including, but not limited to, fluid taken directly from the culture, fluid removed from the culture then subsequently concentrated, or fluid containing antibodies which were previously isolated or purified.

G—a glycine residue.

Heterogeneity—a phenomena wherein secreted antibodies have various discrete biochemical forms, such as, but not limited to, an extra amino acid or acids on the carboxy terminus of one or both of the antibody heavy chains.

Heterogeneous antibodies—antibodies which display various discrete biochemical forms, such as an extra amino acid or acids on the carboxy terminus of one or both of the antibody heavy chains.

Hybridoma—a cell or cell line which secretes a monoclonal antibody, said cell line produced by the fusion of myeloma cells and spleen cells from a suitably immunized animal.

K—a lysine residue.

P—a proline residue.

Primary homogeneous form—the form wherein the carboxy-terminus of the antibody heavy chains contain no extra amino acids.

Recombinant DNA Cloning Vector—any autonomously replicating or integrating agent, including, but not limited to plasmids, comprising a DNA molecule to which one or more additional DNA segments can be or have been added.

Transfection—the introduction of DNA into a recipient host cell via phage DNA particles.

Transformant—a recipient host cell that has undergone transformation.

Transformation—the introduction of DNA into a recipient host cell that changes the genotype and results in a change in the recipient cell.

DETAILED DESCRIPTION OF THE INVENTION

Figure 1:
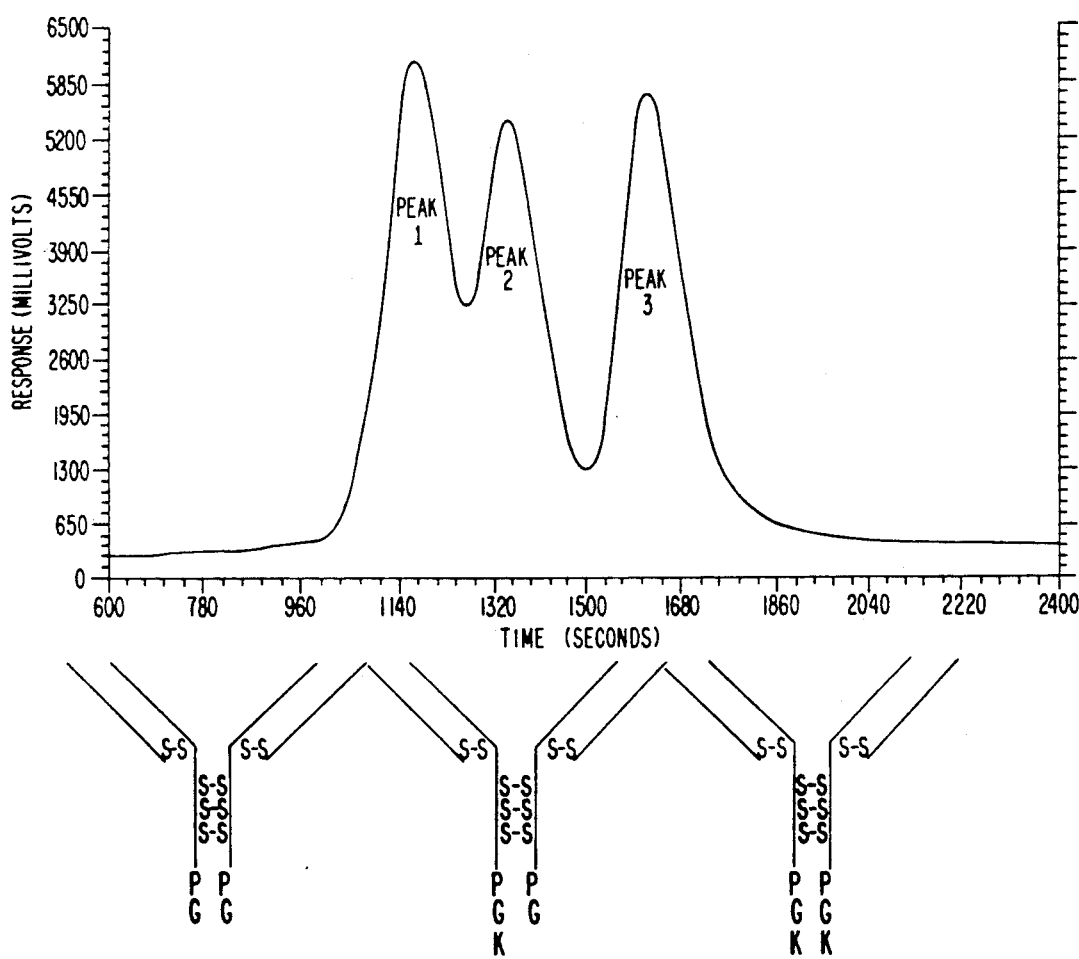
FIG. 1—a schematic showing the differences between the heterogeneous forms of monoclonal antibody CEM231.

The present invention is a method of reducing the heterogeneity of secreted antibodies from antibody-producing cells, said method comprising the alteration of the carboxy-terminal amino acid or acids from one or both of the antibody heavy chains. The invention is best exemplified by the selective removal of an amino acid or amino acids from the carboxy-terminus of one or both heavy chains of an antibody. One method for producing this desired result comprises lowering the pH of a culture fluid containing secreted antibodies to a pH sufficient to reduce the heterogeneity of said antibodies then incubating the culture fluid for a length of time and at a temperature sufficient to allow the reduction of heterogeneity of the antibodies. Generally, the pH may be lowered to a pH between pH ~3.0 and pH ~5.5, although the reaction may occur more efficiently between pH ~3.5 and pH ~4.5. The reaction occurs even more efficiently at a pH of between pH ~4.0 and pH ~4.5, while the preferred pH for reduction of heterogeneity of many antibodies is pH ~4.0.

The temperature and length of the incubation also effects the rate of removal of the carboxy-terminal amino acid or amino acids from the heavy chains of heterogeneous antibodies. The length of the incubation may be anywhere from a few seconds to a number of days, although it is preferable to allow the reaction to occur between ~1 to ~72 hours. In many instances, it may be more preferable to allow the reaction to run between ~4 to ~24 hours. However depending upon the biochemical characteristics of the antibody and the other parameters of the reactions, the incubation may be ~95% complete in only ~24 hours, or it could take up to between ~48 to ~72 hours. The incubation temperature can cover a wide range, although the reaction occurs best between ~2° C. and ~37° C. The reaction also occurs favorably between ~4° C. and ~37° C. and also between ~4° C. and ~30° C. The most preferred reaction temperature range for many antibodies is between ~4° C. and ~25° C., while the most preferred temperature is ~25° C.

Another method for reducing the heterogeneity of secreted antibodies comprises adding ascites fluid to a culture fluid containing secreted antibodies at a volume sufficient to reduce the heterogeneity of said antibodies then incubating the culture fluid for a length of time and at a temperature and pH sufficient to allow the reduction of heterogeneity of the antibodies. While a wide range in volumes of ascites fluid may cause the reaction to occur, it is more efficient to use a mixture wherein the ascites fluid is added at an ~2:1 to ~1:20 volume of ascites fluid to culture fluid. For speed and completeness of the reaction, it is better to add the ascites fluid to an ~1:1 to ~1:10 volume, and better yet to add the ascites fluid to an ~1:1 to ~1:2 volume. The preferred reaction should contain an ~1:1 volume of ascites fluid to culture fluid.

The length of incubation, temperature of incubation and pH of the culture fluid also effect the speed and efficiency of the ascites method mentioned above. Favorable incubation times range from a few seconds to many days, but the reaction is more efficient if the time ranges between ~1 and ~72 hours. Often the reaction is more favorable if the incubation time is between ~16 and ~72 hours, and even better if between ~16 and ~48 hours. The most preferred reaction time is ~16 hours. The temperature of the reaction can cover an almost limitless range, but it is more efficient if the temperature is between ~2° C. and ~42° C. The reaction is more favorable if the temperature is between ~2° C. and ~37° C., and is even better if between ~26° C. and ~37° C. The most preferred temperature of the reaction is ~37° C. The pH of the culture fluid can also speed up or slow down the reaction, and is also important in preventing dissociation of the antibodies. The culture pH can vary over a wide range, but is quite efficient if between pH ~4.0 and pH ~9.0. The reaction works better if between pH ~7.5 and pH ~8.5 and even better if between pH ~7.5 and pH ~8.0. The most preferred pH of the culture fluid is pH ~7.5, therefore, in contrast to the low pH method, this ascites fluid method may be practiced at physiological pH.

Yet another method for reducing the heterogeneity of secreted antibodies comprises adding carboxy peptidase to culture fluid containing the secreted antibodies at a CPIP ratio sufficient to reduce the heterogeneity of said antibodies then incubating the culture fluid for a length of time and at a temperature and pH sufficient to allow the reduction of heterogeneity of the antibodies. While a wide range of CPIP ratios will cause the reaction to occur, it is more efficient to use a CPIP ratio between ~0.01 and ~10.0. It is better to run the reaction at a CPIP ratio of between ~0.2 and ~8.0, and better still to use a CPIP ratio of between ~0.2 and ~1.0. In general the CPIP ratio of ~0.4 is most preferred although skilled artisans will recognize that a higher level of enzyme will cause the reaction to occur at a higher rate. Skilled artisans will also recognize that many different types of carboxypeptidase, such as CpA, CpB, CpC, CpG, CpP, CpW, CpY and others, are well known in the art and can all be used in the method of the present invention. Furthermore, the units of carboxypeptidase are standardized and well known in the art, therefore the practice of this invention is in no way limited to the units defined by any given supplier of carboxypeptidase. Skilled artisans will also recognize that the enzyme may be immobilized to a solid support to avoid having to remove the enzyme during purification.

The length of incubation, temperature of incubation and pH of the culture fluid also effect the speed and efficiency of the carboxypeptidase method mentioned above. Favorable incubation times range from a few seconds to several days, but the reaction is more efficient if the time ranges between ~1 and ~48 hours. Often the reaction is more favorable if the incubation time is between ~1 and ~24 hours, and even better if between ~1 and ~16 hours. The reaction is yet more favorable if the incubation time is between ~5 and ~16 hours and most favorable if it is ~5 hours. The temperature of the reaction can cover an almost limitless range, but is favorable if the temperature is between ~1° C. and ~42° C. The reaction is more favorable if the temperature is between ~15° C. and ~37° C. and even more favorable if between ~20° C. and ~30° C. The most preferred reaction temperature is ~23° C. The pH of the culture fluid can also speed up or slow down the reaction and can vary over a wide range, but is efficient if between pH ~6.0 and pH ~9.0. The reaction works better if between pH ~7.0 and pH ~8.0 and even better still if between pH ~7.5 and pH ~8.0. The most preferred pH of the culture fluid is ~7.5.

Skilled artisans will recognize that by altering the pH of the culture fluid, length of incubation, temperature of incubation, ascites fluid ratios or CPIP ratios, any of the above methods may be fitted to the need of any immunoglobulin purification scheme. Following the reduction of heterogeneity reaction, the antibodies can be isolated in reduced heterogeneous form from the culture fluid using methods which are well known in the art. Skilled artisans will readily recognize that the above-mentioned methods may also be used to reduce the heterogeneity of antibodies which have already been purified.

Essentially the same result may be obtained by a variety of other chemical treatments which remove the carboxy-terminal residue from a peptide. For example, in selected cases, hydrazinolysis, tritiation, and hydantoin formation followed by treatment with acetohydroxamic acid will also be useful. Virtually any chemical reaction which removes a peptide or peptides from the carboxy terminus of an immunoglobulin fragment would fall within the scope of the present invention. Specifically, dipeptidyl carboxypeptidases that remove dipeptides from the carboxy-terminus would also be useful in practicing the present method, as would any other enzyme that can specifically cleave in the carboxy-terminal region internal to the lysine residue.

Yet another method of practicing the present invention arises from the selective removal of the codon or codons which encode the carboxy-terminal lysine or lysines from the gene which encodes the immunoglobulin heavy chain. Skilled artisans recognize that once the DNA sequence encoding an antibody is deduced, then it is a matter of ordinary skill to use recombinant DNA techniques to remove the codon or codons which encode the carboxy-terminal peptides. Upon expression of this truncated gene in a transfected or transformed cell, the gene product will comprise an antibody chain which differs from the wild type antibody chain only in the removal of the carboxy-terminal peptide. Alternatively, recombinant DNA techniques can also be used to add codons encoding different residues to the carboxy-terminus of the polypeptide, thereby changing the charge of the carboxy-terminus and reducing the heterogeneity of the antibody population. Therefore any manipulation, whether chemical or biological, which alters the carboxy-terminus of an antibody and thereby reduces the heterogeneity of the antibody population, is within the scope of the present invention.

The preferred embodiment of the present invention is best exemplified by the conversion of monoclonal antibody CEM231. Monoclonal antibody CEM231 is secreted from hybridoma CEM231.6.7, a strain deposited and part of the permanent stock culture collection of the American Type Culture Collection (ATCC), 12301 Parklawn Drive, Rockville, Md. 20852. It is available to the public as a source and stock reservoir of the antibody under the accession number ATCC HB 9620.

After growth of the hybridoma in serum-free media, the cell-free culture was concentrated 40-115X, then the pH of the fluid was reduced to pH 4.0 by titration with $H_3PO_4$. Following incubation of the fluid for 24 hours at 25° C., greater than 95% of the antibodies in the culture fluid were converted into the primary homogeneous form. This primary homogenous form, as evidenced by cation exchange chromatography, is the form wherein the carboxy-terminus of the antibody chains contain no extraneous amino acids. Furthermore, the efficacy of this conversion method may, in some cases, be increased by the addition of a chelating agent, such as EDTA (1-10 mM), to the reaction mixture.

The ascites fluid method can also be used to convert heterogeneous CEM231 into the primary homogeneous form. The concentrated CEM231 culture fluid was mixed in a 1:1 volume ratio with ascites fluid, then incubated at 37° C. at a pH of 7.4. This reaction converted the nearly equimolar concentrations of heterogeneous antibody into greater than 80% primary homogeneous antibody in a period of 16 hours. The efficacy of this conversion method may, in some cases, be increased by the addition of a chelating agent, such as EDTA (1-10 mM), to the reaction mixture. Any ascites fluid may be utilized for the conversion process, although it is preferable to use a type which contains an antibody with substantially different biochemical characteristics than the antibody undergoing conversion. The different characteristics will then be useful during the purification process to prevent cross-contamination of the ascites-produced antibodies and the converted antibodies.

The carboxypeptidase method can also be used to convert heterogeneous CEM231 into the primary homogeneous form. After growth of the hybridoma in serum-free media, the cell-free culture was concentrated 70X, then carboxypeptidase B was added to the culture at a CPIP ratio of 3.0. Following incubation of the fluid for 5 hours at 23° C., greater than 95% of the antibodies in the culture fluid were converted to primary homogeneous form.

In addition to the conversion of monoclonal antibody CEM231, the above methods have been used to reduce the heterogeneity of a wide variety of antibodies, both from hybridoma cell lines and transformed or transfected cell lines. Table I presents a representative sampling of the various antibodies tested and results obtained.

TABLE I

| \multicolumn{3}{c}{CONVERSION SUMMARY} |||
|---|---|---|
| Antibody | Method | Results |
| CEV124 | pH4 | >80% peak in 4-24 hours at 4° C. |
| QC1054 | pH4 | 60% peak in 43 hours at 4° C. |
| TSE031 | pH4 (Low Conc) | >80% peak in 48 hours at 4° C. |
| TSE031 | pH4 (High Conc) | >80% peak in 14 hours at 4° C. |
| AFU212 | pH4 | >80% peak in 56 hours at 4° C. |
| ZHB068 | pH4 | >80% peak in 72 hours at 4° C. |
| CEV124 | Ascites | >80% peak in 16 hours at 37° C. |
| QC1054 | Ascites | 69% peak in 24 hours at 37° C. |
| HCU061 | Ascites | >80% peak in 17 hours at 37° C. |
| CEV124 | CP | >80% peak in 5 hours at 23° C. |
| QC1054 | CP | >80% peak in 16 hours at 22° C. |
| CEM231 Chimeric | CP | >80% peak in 16 hours at 22° C. |
| CEM231/ CHA255 Bifunctional | CP | >80% peak in 16 hours at 22° C. |

Skilled artisans will readily recognize that the methods of the present invention are also useful for reducing the heterogeneity of antibodies produced from cells other than hybridomas. Specifically, the genes which encode a monoclonal antibody can be ligated into a variety of recombinant DNA cloning vectors, then transformed or transfected into appropriate host cells, including bacteria or yeast. Under proper conditions, the transformed or transfected cells will then produce and secrete the monoclonal antibody. Chimeric antibodies, which contain variable regions from one species joined to the constant regions from a second species, may also be constructed and expressed in recombinantly transformed or transfected host cells. See Boulianne et al., 1984, Nature 312:643-646, the teaching of which is herein incorporated by reference. Furthermore, the method of the present invention is useful to reduce the heterogeneity of human antibodies or bifunctional antibodies. The methods of the present invention may also be used to reduce the heterogeneity of antibodies isolated from blood, serum or other bodily fluids.

Those skilled in the art will also understand that many different compounds may be employed to lower the pH of the culture fluid and that all such equivalents fall within the scope of the present invention. When using the ascites method, many different ratios of antibody culture fluid to ascites fluid may be employed and all such equivalents fall within the scope of the present invention. Furthermore, when using the carboxypeptidase method to reduce the heterogeneity of antibodies, many CPIP ratios may be employed, all of which fall within the scope of the present invention. In addition, the length and temperature of incubation and pH of the culture fluid needed for optimal conversion will vary according to the exact biochemical characteristics of the antibody employed. It may also be advantageous to concentrate the culture fluid before beginning the conversion process, but the novel methods work on both concentrated and dilute samples, therefore the invention is not limited by the sample concentration.

Hybridomas and other antibody secreting cell lines may be grown in flasks or in continuous flow fermentation tanks. Serum-free media may be used, and the pH of the culture is maintained between the range of about 6.5 to 8.5 at temperatures ranging from 30° C. to 40° C. Each antibody-secreting cell line requires its own optimal conditions which should be readily discernable by the skilled artisan.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for practicing the invention are described where appropriate.

EXAMPLE 1

Culture of Hybridoma CEM231.6.7

Hybridoma CEM231.6.7, which secretes monoclonal antibody CEM231, is obtained from the American Type Culture Collection (ATCC), 12301 Parklawn Drive, Rockville, Md. 20852. Hybridoma CEM231.6.7 is part of the permanent stock culture collection of the ATCC and is available to the public as a source and stock reservoir of the antibody under the accession number ATCC HB9620. Frozen cells are allowed to thaw quickly, then are immediately washed with about 10 ml of HL1 media supplemented with 4 mM glutamine. HL1 media is purchased from Ventrex of Portland, Me. The cells are placed in a T flask and incubated until high cell density is attained.

Two 250 ml spinner bottles containing HL1 media supplemented with 4 mM glutamine were seeded at about 300,000 cells per millileter with CEM 231.6.7 cells which were secreting antibody. The cells were allowed to incubate at 37° C. for about 48 hours until the cell density reached about 900,000 cells per milliliter. Another aliquot of glutamine was then added to each spinner to bring the final concentration of the culture up to 4 mM glutamine. The spinners containing the CEM231.6.7 cells were then allowed to incubate at 37° C. for another eight to ten days.

After the final incubation, the cell culture was poured into two 250 ml bottles and centrifuged at about 10,000 rpm for twenty minutes in a Beckmann JA8 rotor in a Beckmann J2-21 centrifuge. About 375 ml of supernatent was recovered and preliminary quantification indicated that the antibody concentration was about 80 μg per milliliter. The culture fluid was then concentrated to about 40 ml using a 400 ml stirred cell concentrator equipped with a YM10 76 mm filter (available from the Amicon Corporation, Scientific Systems Division, 21 Hartwell Avenue, Lexington, Mass. 02173). The 40 ml culture was further concentrated to approximately 3.27 ml by using a 50 ml Amicon stirred cell concentrator equipped with a YM10 filter. The concentrated supernatent was finally filtered through a 1.2 μm 25 mm Acrodisc. This collected supernatent can be frozen at −70° C., if needed.

EXAMPLE 2

Conversion of Antibody CEM231 Using the Low pH Method

Antibody CEM231, cell-free concentrate was adjusted to pH 4.0 by titration with 1N $H_3PO_4$. The sample was then incubated for 24 hours at 25° C. and the heterogeneity was assessed by cation exchange chromatography on a Mono-S HR 5/5 column, pH 4.5 in 0.17 M sodium acetate buffer with a gradient of 0.0-0.2 M NaCl. Experimental data demonstrated that after 24 hours there was no detectable heterogeneity remaining in the sample.

EXAMPLE 3

Conversion of Antibody CEM231 Using Ascites Fluid

Ascites fluid was isolated from ascites fluid-producing mice in substantial accordance with the teaching of Galfrè and Milstein, (1981) Methods in Enzymology 73:43-44, the the teaching of which is herein incorporated by reference. Aliquots of purified monoclonal antibody CEM231 containing about 200 μg antibody per aliquot were mixed with the ascites fluid in a 1:2 ascites fluid/antibody culture fluid ratio. The sample was incubated at 24° C. for 24 hours and the heterogeneity was assessed by cation exchange chromatography on a Mono-S HR 5/5 column, pH 4.4 in 0.17 M sodium acetate buffer with a gradient of 0.0-0.2 M NaCl. Experimental data demonstrated that after 24 hours greater than 80% of the antibodies had been converted into the primary homogeneous form, while control samples incubated without ascites fluid remained nearly equimolar in all three heterogeneous forms.

EXAMPLE 4

Conversion of Antibody CEM231 Using the CP Method

An approximately 5 mg aliquot of the antibody CEM231 concentrate was incubated at 23° C. for 5 hours with about 50 μg carboxypeptidase B. Carboxypeptidase B was purchased from Calbiochem, P.O. Box 12087, San Diego, Calif. 92112 and has an enzyme activity of 295 IU/mg. This reaction therefore corresponded to a CPIP ratio of approximately 3.0. After the 5 hours incubation, the heterogeneity of the sample was assessed by cation exchange chromatography on a Mono-S HR 5/5 column, pH 4.5 in 0.17 M sodium acetate buffer with a gradient of 0.0- 0.2M NaCl. Experimental data demonstrated that greater than 95% of the antibodies within the sample had been converted to the primary homogeneous form, while untreated antibodies retained an almost equimolar ratio of the heterogeneous forms.

We claim:

1. A method of reducing the heterogeneity of secreted antibodies from antibody-producing cells, said method comprising
   a) Subjecting said antibodies to a proteolytic enzyme, ascites fluid or low pH to remove an amino acid or amino acids from the carboxy-terminus of one or both of the antibody heavy chains; or b) using recombinant DNA techniques to add an amino acid or amino acids to the carboxy-terminus of one or both of the antibody heavy chains.

2. The method of claim 1 which comprises the removal of the carboxy-terminal amino acid or acids from one or both of the antibody heavy chains.

3. The method of claim 2 which comprises:
a) adding carboxypeptidase to a culture fluid containing the secreted antibodies at a CPIP ratio sufficient to reduce the heterogeneity of said antibodies,
b) incubating said culture fluid for a length of time and at a temperature and pH sufficient to allow the reduction of heterogeneity of said antibodies,
then isolating said antibodies in a reduced heterogeneous form from the culture.

4. The method of claim 3 wherein the CPIP ratio is between ~0.01 and ~10.0.

5. The method of claim 4 wherein the length of incubation is between ~1 and ~48 hours.

6. The method of claim 5 wherein the temperature of incubation is between ~1° C. and ~42° C.

7. The method of claim 6 wherein the pH of the culture fluid is between pH ~6.0 and ~9.0.

8. The method of claim 7 wherein the CPIP ratio is between ~0.2 and ~8.0.

9. The method of claim 8 wherein the length of incubation is between ~1 and ~24 hours.

10. The method of claim 9 wherein the temperature of incubation is between ~15° C. and ~37° C.

11. The method of claim 10 wherein the pH of the culture fluid is between pH ~7.0 and pH ~8.0.

12. The method of claim 11 wherein the CPIP ratio is between ~0.2 and ~1.0.

13. The method of claim 12 wherein the length of incubation is between ~1 and ~16 hours.

14. The method of claim 13 wherein the temperature of incubation is between ~20° C. and ~30° C.

15. The method of claim 14 wherein the pH of the culture fluid is between pH ~7.5 and pH ~8.0.

16. The method of claim 11 wherein the CPIP ratio is ~3.0.

17. The method of claim 16 wherein the length of incubation is between ~5 and ~16 hours.

18. The method of claim 17 wherein the temperature of incubation is ~23° C.

19. The method of claim 18 wherein the pH of the culture fluid is ~7.5.

20. The method of claim 19 wherein the length of incubation is ~5 hours.

21. The method of claim 2 which comprises:
a) adding ascites fluid to a culture fluid containing secreted antibodies at a volume sufficient to reduce the heterogeneity of said antibodies,
b) incubating said culture fluid for a length of time and at a temperature and pH sufficient to allow the reduction of heterogeneity of said antibodies,
then isolating said antibodies in a reduced heterogeneous form from the culture.

22. The method of claim 21 wherein the ascites fluid is added at an ~2:1 to ~1:20 volume of ascites fluid to culture fluid.

23. The method of claim 22 wherein the length of incubation is between ~1 to ~72 hours.

24. The method of claim 23 wherein the temperature of incubation is between ~2° C. and ~42° C.

25. The method of claim 24 wherein the pH of the culture fluid is between pH ~4.0 and pH ~9.0.

26. The method of claim 25 wherein an ~1:1 to ~1:10 volume of ascites fluid is added to the culture fluid.

27. The method of claim 26 wherein the length of incubation is between ~16 to ~72 hours.

28. The method of claim 27 wherein the temperature of incubation is between ~2° C. and 37° C.

29. The method of claim 28 wherein the pH of the culture fluid is between pH ~7.5 and pH ~8.5.

30. The method of claim 29 wherein an ~1:1 to ~1:2 volume of ascites fluid is added to the culture fluid.

31. The method of claim 30 wherein the length of incubation is ~16 to ~48 hours.

32. The method of claim 31 wherein the temperature of incubation is between ~26° C. and 37° C.

33. The method of claim 32 wherein the pH of the culture fluid is between pH ~7.5 and pH ~8.0.

34. The method of claim 33 wherein an ~1:1 volume of ascites fluid is added to the culture fluid.

35. The method of claim 34 wherein the length of incubation is ~16 hours.

36. The method of claim 35 wherein the temperature of incubation is ~37° C.

37. The method of claim 36 wherein the pH of the culture fluid is pH ~7.5.

38. The method of claim 2 which comprises:
a) lowering the pH of a culture containing secreted antibodies to a pH sufficient to reduce the heterogeneity of said antibodies,
b) incubating said culture fluid for a length of time and at a temperature sufficient to allow the reduction of heterogeneity of said antibodies,
then isolating said antibodies in a reduced heterogeneous form from the culture.

39. The method of claim 38 wherein the pH of the culture is lowered to between pH ~3.0 and pH ~5.5.

40. The method of claim 39 wherein the length of incubation is between ~1 and ~72 hours.

41. The method of claim 40 wherein the temperature of incubation is between ~2° C. and ~37° C.

42. The method of claim 41 wherein the pH of the culture fluid is lowered to between pH ~3.5 and pH ~4.5.

43. The method of claim 42 wherein the length of incubation is between ~4 and ~48 hours.

44. The method of claim 43 wherein the temperature of incubation is between ~4° C. and ~37° C.

45. The method of claim 44 wherein the pH of the culture fluid is lowered to between pH ~4.0 to pH ~4.5.

46. The method of claim 45 wherein the length of incubation is between ~4 to ~24 hours.

47. The method of claim 46 wherein the temperature of incubation is between ~4° C. and ~30° C.

48. The method of claim 47 wherein the pH of the culture fluid is lowered to pH ~4.0.

49. The method of claim 48 wherein the length of incubation is ~24 hours.

50. The method of claim 49 wherein the temperature of incubation is ~25° C.

51. The method of claim 50 wherein the temperature of incubation is ~4° C.

52. The method of claim 45 wherein the length of incubation is between ~12 and ~24 hours.

53. The method of claim 39 wherein the length of incubation is between ~48 and ~72 hours.

54. The method of claim 53 wherein the pH of the culture fluid is lowered to between pH ~4.0 and pH ~4.5.

55. The method of claim 54 wherein the temperature of incubation is between ~4° C. and ~25° C.

56. The method of claim 55 wherein the length of incubation is between ~50 and ~72 hours.

57. The method of claim 56 wherein the pH of the culture fluid is lowered to pH ~4.0.

58. The method of claim 57 wherein the temperature of incubation is ~4° C.

59. The method of claim 58 wherein the length of incubation is between ~56 and ~72 hours.

60. The method of claim 59 wherein the length of incubation is ~72 hours.

61. The method of claim 1 wherein the secreted antibodies are selected from the group consisting of chimeric, bifunctional, and human monoclonal antibodies.

62. The method of claim 2 wherein the enzyme responsible for the removal of the carboxy-terminal amino acid or acids is immobilized.

63. The method of claim 21 wherein the ascites fluid is immobilized.

* * * * *